United States Patent [19]
Parks

[11] Patent Number: 5,642,530
[45] Date of Patent: Jul. 1, 1997

[54] NON-FOGGING GOGGLES

[75] Inventor: Gerald R. Parks, Chula Vista, Calif.

[73] Assignee: John R. Gregory, Bonita, Calif.

[21] Appl. No.: 642,647

[22] Filed: May 3, 1996

[51] Int. Cl.⁶ ............................................. A61F 9/02
[52] U.S. Cl. ................................................. 2/435; 2/434
[58] Field of Search ........................... 2/435, 434, 441, 2/443, 426, 424, 9

[56] References Cited

U.S. PATENT DOCUMENTS

| | | | |
|---|---|---|---|
| 2,427,918 | 9/1947 | Malcom et al. | 2/441 |
| 3,081,461 | 3/1963 | Gurtowski | 2/441 |
| 4,047,249 | 9/1977 | Booth | 2/434 X |
| 4,138,746 | 2/1979 | Bergmann | 2/434 X |
| 4,414,693 | 11/1983 | Brody | 2/435 |
| 4,682,007 | 7/1987 | Hollander | 2/435 X |
| 4,972,521 | 11/1990 | Lison | 2/435 X |

*Primary Examiner*—Peter Nerbun
*Attorney, Agent, or Firm*—Henri J. A. Charmasson; John D. Buchaca

[57] ABSTRACT

A non-fogging goggle assembly comprises a transparent film of polyester or polycarbonate coated with a hydrophilic composition that lowers the surface tension of water droplets, causing them to spread rather than form vision-obstructing beads. The film is applied against the inner face of the goggle lens and releasably held in place without any adhesive by pressure-fitting the edge of the film or parts thereof into peripheral slots or grooves cut into the section of the frame surrounding the lens.

8 Claims, 1 Drawing Sheet

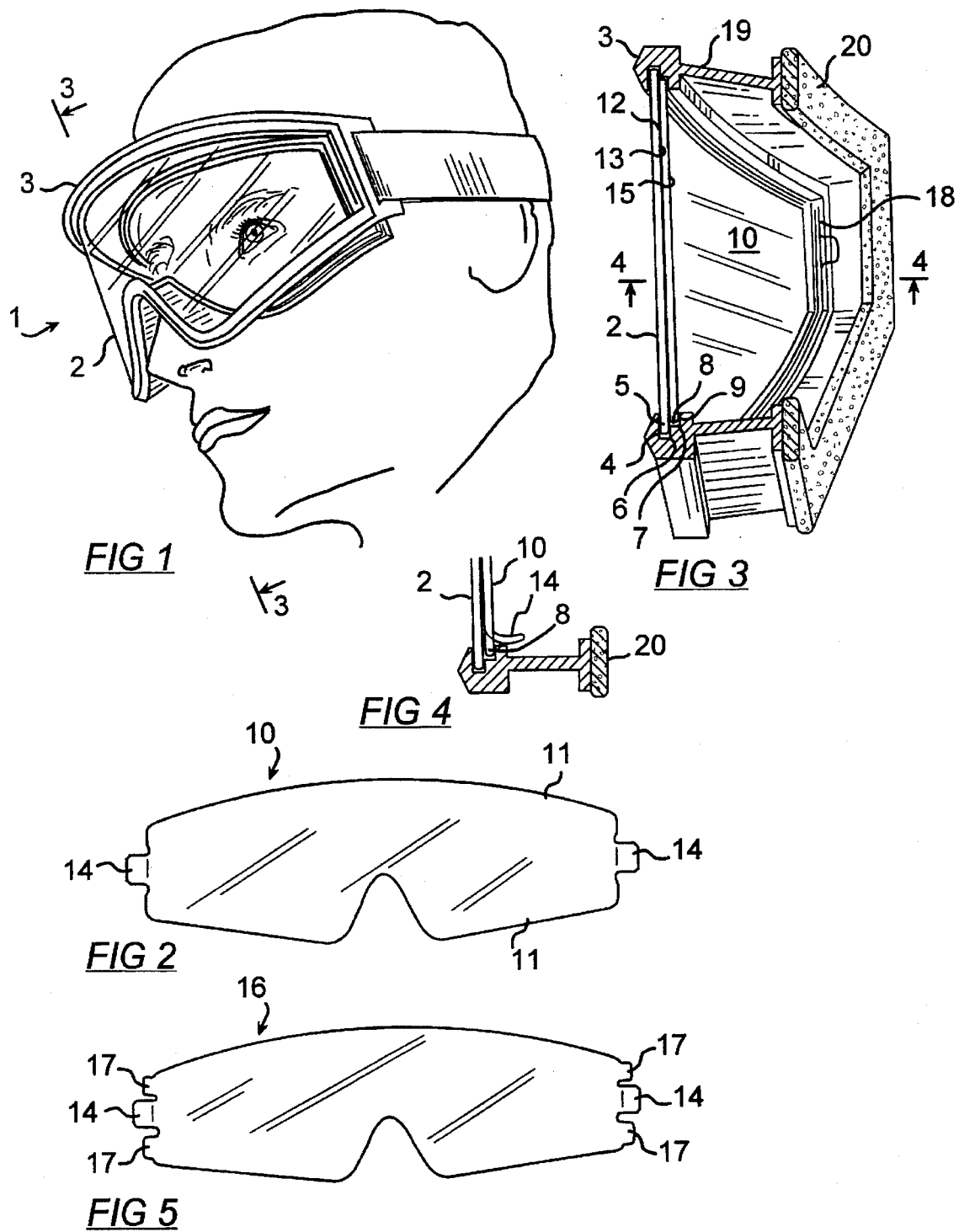

NON-FOGGING GOGGLES

FIELD OF THE INVENTION

This invention relates to eyewear, and more particularly to protective eyewear such as goggles used in the practice of skiing, snowboarding, motorcycle racing, paintball games, and other such activities where perspiration and breathing is conducive to the accumulation of moisture against the inner face of the goggle lens.

BACKGROUND OF THE INVENTION

Moisture accumulation against the inner face of goggle lenses resulting from the wearer's perspiration and breathing can result in the formation of vision-impairing beads which are a great inconvenience to skiers, motorcyclists, paintball game players and the practitioners of similar demanding sports activities. Fogging inside goggles can be reduced by multi-layered lenses and reflective coating as disclosed in U.S. Pat. No. 5,018,223 Dawson et al. The inner face of the goggle lens can also be coated with an hydrophilic composition which lowers the surface tension of water droplets causing them to spread rather than form vision-impairing beads. Polyester films coated with such a composition as the one disclosed in U.S. Pat. No. 4,467,073 are provided with sticky backing so that they can be glued against the inner surface of the goggle's lens. Sheets of such films are commercially available under the mark VISTEX from FILM SPECIALITIES, INC. of Whitehouse, N.J.

Since the exposed, coated surface of such a film is less resistant to abrasion than the material used in the fabrication of the goggle lens, the useful life of the goggle tends to be reduced due to early scratching of the film surface. Replacement of the anti-fogging film is impractical, and often yields less than desirable results due to the fact that part of the adhesive of the removed film tends to remain against the inner face of the lens. In practice, the entire lens and anti-fogging film assembly has to be replaced.

When the goggles are used in a highly moisture-laden environment, or when worn by subjects prone to a high level of perspiration, the entire fogging film tends to saturate with moisture and loses it anti-fogging properties. Unless the goggles provides for quick replacement of the lens assembly, the user is forced to replace the blurred goggles with a new set.

It would be advantageous to be able to quickly replace the saturated anti-fogging film in the middle of a sporting activity.

SUMMARY OF THE INVENTION

The principal and secondary objects of this invention are to provide a practical and rapid way to replace the anti-fogging film used in connection with goggles, while reducing the labor involved in applying anti-fogging films to the inner surface of the goggles.

These and other desirable objects are achieved by force-fitting a section of anti-fogging film directly against the inner face of the goggle lens, without using any adhesive.

BRIEF DESCRIPTION OF THE DRAWING

FIG. 1 is a perspective view of goggles according to the invention;

FIG. 2 is a front elevational view of a anti-fogging film;

FIG. 3 is a cross-sectional view taken along line 2—2 of FIG. 1;

FIG. 4 is a partial cross-sectional view taken along line 4—4 of FIG. 3; and

FIG. 5 is a front elevational view of an alternate embodiment of the anti-fogging film.

DESCRIPTION OF THE PREFERRED EMBODIMENT OF THE INVENTION

Referring now to the drawing, there is shown in FIG. 1, goggles 1 of the type used in connection with the practice of skiing, snowboarding, motorcycle racing, paintball games and other such activities that requires a wide angle of unimpaired vision and good protection against the impact of, paintballs, raindrops, mud, snow, and similar hazards. This particular type of goggles comprises a single arcuate lens 2 made of high-impact plastic. The lens is held in place on the frame 3 by a groove 4 which engages an edge section 5 of the lens around its entire periphery. As illustrated in FIGS. 3 and 4, the lens-holding groove 4 has its deepest half section 6 commensurate in width with the thickness of the lens 2. The second half section 7 of the groove nearest its opening is enlarged to form a slot 8 between the peripheral edge of the lens 5 and the inner wall 9 of the groove 4.

An anti-fogging film 10 having substantially the same shape as the lens 2, but slightly smaller dimensions has its peripehral edge 11 nesting into the slot 8 so that its outer face 12 is applied against the inner face 13 of the lens. The film 10 is held in place against the lens without use of any adhesive between the outer face of the film and the inner face of the lens after having its peripheral edge force-fitted into the slot 8. Basically, the difference between the lengths and width of the lens and film in all sections of those components is equal to the depth of the groove 4. The film 10 has a pair of pull tabs 14 extending from opposite lateral edges. As illustrated in FIG. 4, the pull tabs are not inserted into the film-holding slot. They are folded back against the inner side of the frame 3 where they can be grabbed between thumb and index to peel the film out of its slot when replacement is warranted.

The film 10 is preferably made of transparent polycarbonate or polyester. Its inner face 15 is coated with an hydrophilic composition which reduces the surface tension of moisture droplets which might form on its surface causing them to spread out in a transparent film of moisture rather forming vision-impairing beads.

In the alternate embodiment of the film 16 illustrated in FIG. 5, the dimensions are slightly smaller than those of the frame so that it may be applied against the inner face 13 of the lens without extending into the slot 8 except for the two pairs of end projections 17 astride the pull tabs. This design allows for even quicker removal and replacement of the film than the first embodiment 10. It should be noted that if the goggles are designed to accommodate only the second type of film 16, the enlarged section of the groove 4 forming the slot can be limited to opposite lateral sections 18 of the frame.

It should be noted that althought the goggles described and illustrated in these embodiments of the invention have an enlarged, inwardly located frame section 19 backed by a perspiration-absorbing foam strip 20, the invention can be implemented with any type of eyewear including vision-correcting glasses and other types of single lens and double lens goggles.

While the preferred embodiments of the invention have been described, modifications can be made and other embodiments may be devised without departing from the spirit of the invention and the scope of the appended claims.

What is claimed is:

1. A non-fogging eyewear assembly which comprises:

a transparent lens having inner and outer faces;

a frame having a section surrounding and holding said lens;

an anti-fogging sheet of transparent film releasably held against the inner face of lens in the absence of any adhesive bonding between said lens and said sheet;

finger-actionable means for rapidly peeling said sheet off said inner face; and means for rapidly force-fitting said sheet against said inner face.

2. The eyewear assembly of claim 1, wherein said section of the frame has at least one slot running parallel and proximately to a peripheral edge of the inner face of said lens; and said sheet is shaped and dimensioned to have a peripheral section seating into said at least one slot.

3. The eyewear assembly of claim 2, wherein said section has a groove engaging said peripheral edge.

4. The eyewear assembly of claim 3, wherein said sheet comprises at least two diametrically opposed peripheral projections dimensioned to seat into said at least one slot.

5. The eyewear assembly of claim 4, wherein said at least one slot comprises a pair of diametrically opposed slot sections shaped, positioned and dimensioned to receive said projections when said sheet is forced against the inner face of said lens.

6. The eyewear assembly of claim 3, wherein said sheet comprises:

an outer face in contact with the inner face of said lens and an opposite inner face; and a coat of hydrophilic composition applied to the inner face of said sheet.

7. The eyewear assembly of claim 5, wherein said means for peeling comprise at least one integral peripheral projection shaped and dimensioned to form a pull-tab along an edge of said sheet.

8. A non-fogging eyewear assembly which comprises:

a transparent lens having inner and outer faces;

a frame having a section surrounding and holding said lens;

an anti-fogging sheet of transparent film releasably held against the inner face of the lens in the absence of any adhesive bonding between said lens and said sheet; and wherein:

said section of the frame has at least one slot running parallel and proximately to a peripheral edge of the inner face of said lens and a groove engaging said peripheral edge;

said sheet comprises at least two diametrically opposed peripheral projections dimensioned to seat into said at least one slot;

said sheet comprises at least one pull-tab along an edge of said sheet; and a pair of said projections located along each lateral edge of said sheet, and one of said pull-tabs located between projections of each of said pairs.

* * * * *